(12) United States Patent
Takai et al.

(10) Patent No.: US 8,895,799 B2
(45) Date of Patent: Nov. 25, 2014

(54) ABSORBER FORMING CROSSBRIDGE UPON ABSORBING

(75) Inventors: Hisashi Takai, Kagawa (JP); Takayoshi Konishi, Kagawa (JP); Masashi Nakashita, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 738 days.

(21) Appl. No.: 12/933,582

(22) PCT Filed: Mar. 26, 2009

(86) PCT No.: PCT/JP2009/056035
§ 371 (c)(1),
(2), (4) Date: Sep. 20, 2010

(87) PCT Pub. No.: WO2009/122989
PCT Pub. Date: Oct. 8, 2009

(65) Prior Publication Data
US 2011/0028928 A1 Feb. 3, 2011

(30) Foreign Application Priority Data
Mar. 31, 2008 (JP) ................................. 2008-093485

(51) Int. Cl.
*A61F 13/15* (2006.01)
*A61L 15/42* (2006.01)
(Continued)

(52) U.S. Cl.
CPC ................ *A61F 13/53* (2013.01); *A61L 15/42* (2013.01); *C08L 5/00* (2013.01);
(Continued)

(58) Field of Classification Search
CPC ........... A61F 13/8405; A61F 13/15203; A61F 13/15211; A61F 13/53; A61F 13/532; A61F 2013/8452

USPC .......................................... 604/358, 368, 367
See application file for complete search history.

(56) References Cited

U.S. PATENT DOCUMENTS 3,528,421 A * 9/1970 Roberts et al. ................. 604/372
3,903,889 A * 9/1975 Torr ............................... 604/365
(Continued)

FOREIGN PATENT DOCUMENTS

| EP | 0 137 608 A2 | 7/1984 |
| EP | 0 227 553 A2 | 7/1987 |

(Continued)

OTHER PUBLICATIONS

International Search Report from corresponding PCT application No. PCT/JP2009/056035 dated Jun. 30, 2009, 2 pgs.
(Continued)

*Primary Examiner* — Lynne Anderson
*Assistant Examiner* — Bradley Philips
(74) *Attorney, Agent, or Firm* — Brinks Gilson & Lione (57) ABSTRACT

Provided are an absorbent and an absorptive article containing the absorbent which has excellent water absorbability and leakage prevention ability, and has an intent to achieve reductions in the weight and thickness of an absorptive article.

The absorbent comprises a polysaccharide that causes a gelation reaction in the presence of a polyvalent metal ion and a source of the polyvalent ion, in which the polyvalent ion is supplied simultaneously with or after dissolution and swelling of the polysaccharide. The absorptive article containing the absorbent can achieve excellent water absorbability and leakage prevention ability and thus reductions in the weight and thickness as the absorptive article.

9 Claims, 2 Drawing Sheets (51) Int. Cl.

| | | |
|---|---|---|
| *C08L 5/00* | (2006.01) | |
| *B01J 20/28* | (2006.01) | |
| *A61F 13/472* | (2006.01) | |
| *A61F 13/53* | (2006.01) | |
| *B01J 20/26* | (2006.01) | |
| *A61F 13/84* | (2006.01) | |
| *A61L 15/28* | (2006.01) | |
| *C08L 5/04* | (2006.01) | |
| *A61F 13/534* | (2006.01) | |
| *B01J 20/22* | (2006.01) | |
| *C08L 5/06* | (2006.01) | |

(52) U.S. Cl.
CPC ....... *B01J 20/2804* (2013.01); *A61F 13/47263* (2013.01); *B01J 20/262* (2013.01); *A61F 13/8405* (2013.01); *A61F 2013/8452* (2013.01); *B01J 20/28023* (2013.01); *A61L 15/28* (2013.01); *B01J 20/28045* (2013.01); *C08L 5/04* (2013.01); *A61F 13/534* (2013.01); *B01J 20/223* (2013.01); *C08L 5/06* (2013.01)
USPC .......................................... 604/367; 604/368

(56) References Cited

U.S. PATENT DOCUMENTS

| | | | | |
|---|---|---|---|---|
| 4,145,464 | A * | 3/1979 | McConnell et al. | 428/171 |
| 4,454,055 | A * | 6/1984 | Richman et al. | 252/194 |
| 4,548,847 | A * | 10/1985 | Aberson et al. | 428/74 |
| 4,959,341 | A * | 9/1990 | Wallach | 502/404 |
| 5,847,031 | A * | 12/1998 | Klimmek et al. | 524/44 |
| 6,579,958 | B2 * | 6/2003 | Wilson | 526/185 |
| 6,580,014 | B1 * | 6/2003 | Kasai et al. | 604/368 |
| 8,338,659 | B2 * | 12/2012 | Collins et al. | 604/361 |
| 2012/0115718 | A1 * | 5/2012 | Nakashita et al. | 502/404 |
| 2012/0165773 | A1 * | 6/2012 | Nakashita et al. | 604/364 |

FOREIGN PATENT DOCUMENTS

| | | |
|---|---|---|
| FR | 2 331 603 A1 | 6/1977 |
| FR | 02 843 965 A1 | 3/2004 |
| JP | 60-104503 | 6/1985 |
| JP | 7-59813 | 3/1995 |
| JP | 8-510487 | 11/1996 |
| JP | 9-506798 | 7/1997 |
| JP | 2000-201979 A | 7/2000 |
| JP | 2004-08867 A | 7/2004 |
| JP | 2006-326502 | 12/2006 |
| WO | WO 95/17147 | 6/1995 |
| WO | WO 2006059525 A1 * | 6/2006 |

OTHER PUBLICATIONS

International Preliminary Report on Patentability and Written Opinion from corresponding PCT application No. PCT/JP2009/056035 dated Dec. 13, 2010, 8 pgs.
First Office Action and English translation from corresponding Chinese application No. 200980111726.X dated May 3, 2012, (13 pgs.).
European Search Report from corresponding EP application No. 09727360.1 dated Feb. 5, 2013, 8 pgs.

* cited by examiner

ABSORBER FORMING CROSSBRIDGE UPON ABSORBING

RELATED APPLICATION

This application is a 35 U.S.C. §371 national phase filing of International Patent Application No. PCT/JP2009/056035, filed Mar. 26, 2009, through which and to which priority is claimed under 35 U.S.C. §119 to Japanese Patent Application No. 2008-093485, filed Mar. 31, 2008.

TECHNICAL FIELD

The present invention relates to an absorbent in which a crosslink is formed by water absorption, thereby becoming possible to retain water, and an absorptive article containing the absorbent.

BACKGROUND ART

An absorbent and an absorptive article including the absorbent such as disposable diapers, sanitary products, medical blood absorbing articles, and pet care goods are used for the purpose of treating body fluids or excreta, and required to have excellent absorbability. The absorbent and absorptive article including the absorbent have been researched so as to achieve reductions in the weight and thickness of the article. Furthermore, from the viewpoint of environmental consideration or from the aspect of good hygiene, there has been studied water-disintegrable and biodegradable products which can achieve a reductions in an incineration amount and can be flushed down a toilet after use.

An acrylic acid-based absorbent material made of a synthetic resin which can absorb water in an amount from several tens to several thousands times of its own weight is known as an absorbent material serving as an absorbent. In particular, a product obtained by dispersing particles of a high water-absorption resin made of a polyacrylate-crosslinked product in a pulp fiber is widely used. In the case of the acrylic acid-based absorbent material, a liquid or fluid substance such as a body fluid or excreta is absorbed and retained and fixed in the material only after the liquid or fluid substance arrives at the position existing the absorbent material. Therefore, it takes time to bring all of the liquid or fluid substance to the position, and the liquid leakage may be occurred until the liquid arrives at the position.

Though the acrylic acid absorbent exhibits a very large absorbing amount for ion-exchange water, the amount is largely lowered for ion-containing liquid such as a body fluid. In order to enhance the absorbability, an attempt to lower a crosslinking degree has been made, but the attempt lowers the gel strength, which is quite problematic in practical use.

Until now, an absorbent including a polysaccharide has been studied as an absorbent including no acrylic acid-based absorbent material. For example, there has been proposed a film-like water absorbent material formed by crosslinking a cellulose derivative or a salt thereof with a crosslinking agent, in which the amount of water absorption to 0.9% physiological saline is 10 times or more its own weight, and the gel strength in a state where the aqueous solution is absorbed twenty times its own weight is $3,000 \times 10^{-7} N/mm^2$ or more, and an absorptive article including the film-like water absorbent material (Patent document 1). In addition, there has been also proposed a biodegradable and high-absorbent resin composition obtained by mixing sodium alginate, a carboxylated derivative thereof, or a mixture thereof with a synthetic polymer electrolyte at a weight ratio of 20:80 to 99:1 (Patent document 2). Furthermore, there has been proposed an article for thickening body fluids or excreta which contains a polysaccharide capable of being thickened in the presence of a polyvalent metal ion, the polysaccharide being present in a state ready to dissolve or be dissociated in the aqueous component in body fluids or excreta (Patent document 3).

However, in the film-like water absorbent material and water absorptive article containing the material disclosed in Patent document 1, a crosslink is formed with a crosslinking agent before use same as in the case of a conventional granular high water-absorbent resin, and the crosslink thus lowers the amount of water absorbed in the material. Therefore, it is necessary to use a large amount of the absorbent material for keeping the amount of water absorbed in the product, resulting in increases in the mass/thickness of the absorbent although the material and article are film-like products. In addition, as the film-like absorbent is a cellulose derivative, there are problems that it is difficult to obtain electrostatic repulsion in the polymer chain and adsorption is slow compared to a general high water-absorbent resin.

The biodegradable and high absorbent resin composition obtained by mixing sodium alginate, a carboxylated derivative of sodium alginate, or a mixture thereof with a synthetic polyelectrolyte, disclosed in Patent document 2, comprises sodium alginate (carboxylated derivative) and the synthetic polyelectrolyte. Therefore, the absorption amount of the material is lowered by crosslink as described above. Accordingly, it is necessary to use a large amount of an absorbent material for keeping the absorption amount of the product, resulting in increases in the mass/thickness of the absorbent. In addition, there are problems in that static electricity repulsion in the polymer chain is hardly obtained and absorption is slow compared to a general high water-absorbent resin.

The article for thickening body fluids or excreta disclosed in Patent document 3 includes a polysaccharide that is dissolved in the aqueous component in excreta and is capable of being thickened in the presence of a polyvalent metal ion. However, the source of the polyvalent metal ion is only the body fluids or excreta, and the article does not include a source of the polyvalent metal ion. Only the metal ion in excreta cannot provide enough thickening effect, and the article cannot absorb and retain the liquid in a sufficient amount.

[Patent document 1] JP-A-2006-192368
[Patent document 2] JP-A-H06-306298
[Patent document 3] JP-A-2000-201976

DISCLOSURE OF THE INVENTION

An object of the present invention is to provide an absorbent and an absorptive article containing the absorbent, which has excellent water absorbability and leakage prevention ability and may achieve reductions in the weight and thickness of the absorptive article.

The inventors of the present invention have made extensive studies to solve the above-mentioned problems. As a result, the inventors have found that the above-mentioned problems can be solved by using an absorbent comprising both a polysaccharide capable of causing a gelation reaction and being thickened in the presence of a polyvalent metal ion and a substance capable of supplying the polyvalent metal ion, and an absorptive article including the absorbent to absorb and retain a body fluid or liquid excreta quickly even in small amount.

The inventors have reached the inventions of an absorbent which includes a polysaccharide capable of being thickened in the presence of a polyvalent metal ion and a substance capable of supplying the polyvalent metal ion, wherein dissolution of the substance capable of supplying the polyvalent metal ion is started simultaneously with or after dissolution of the polysaccharide capable of being thickened, and an absorptive article where the absorbent is arranged between a liquid-permeable topsheet and a liquid-impermeable backsheet.

That is, the present invention provides:

(1) An absorbent comprising at least a polysaccharide capable of being thickened in a presence of a polyvalent metal ion and a substance capable of supplying the polyvalent metal ion;

(2) The absorbent according to the item (1), in which dissolution of the substance capable of supplying the polyvalent metal ion is started simultaneously with or after dissolution of the polysaccharide;

(3) The absorbent according to the item (1) or (2), in which the polysaccharide is arranged at a position where the polysaccharide is brought into contact with a body fluid before the substance capable of supplying the polyvalent metal ion is brought into contact with a body fluid;

(4) The absorbent according to any of the items (1) to (3), in which the substance capable of supplying the polyvalent metal ion is arranged in the absorbent after treatment for adjusting a dissolution rate;

(5) The absorbent according to any of the items (1) to (4), in which the polysaccharide is arranged in the absorbent in at least one form selected from the group consisting of a foam, a film, a immobilized substrate, powder and a fiber;

(6) The absorbent according to any of the items (1) to (5), in which the polysaccharide comprises at least one selected from the group consisting of sodium alginate, propylene glycol alginate, pectin, gellan gum, carrageenan, glucomannan and guar gum;

(7) The absorbent according to any of the items (1) to (6), in which the substance capable of supplying the polyvalent metal ion is a substance capable of supplying a divalent metal ion;

(8) An absorptive article comprising a liquid-permeable topsheet, a liquid-impermeable backsheet, and the absorbent according to any of the items (1) to (7) located between the both sheets;

(9) The absorptive article according to the item (8), further comprising a material for assisting dispersion and/or water absorption arranged in the absorbent, between the topsheet and absorbent, and/or between the absorbent and backsheet;

(10) The absorptive article according to the item (8) or (9), further having water-disintegrability; and (11) The absorptive article according to any of the items (8) to (10), further having biodegradability.

Effect of the Invention

According to the present invention, it is possible to reduce the use amount of an absorbent material and to achieve reductions in the weight and thickness of the absorptive article because the absorbent of the present invention, which comprises at least a polysaccharide capable of being thickened in the presence of a polyvalent metal ion and a substance capable of supplying the polyvalent metal ion, the polysaccharide can thus be dissolved (swollen) with the liquid in a body fluid or liquid excreta, and simultaneously the polysaccharide thickened with the polyvalent metal ion can absorb a large amount of the body fluid or liquid excreta. Moreover, the polysaccharide capable of being thickened in a presence of a polyvalent metal ion is dissolved before or simultaneously with dissolution of the substance capable of supplying the polyvalent metal ion and crosslinked by the polyvalent metal ion during or after swelling of the polysaccharide to completely retain the body fluid or liquid excreta in a gel state, so the absorbent can lower flowability of the body fluid and liquid excreta and can prevent return of the liquid and leakage of the liquid.

The polysaccharide capable of being thickened in the presence of a polyvalent metal ion may increase the specific surface area by forming into a thin film or foam. As a result, the dissolution rate of the polysaccharide can be increased to surely prevent leakage of a liquid. The film or foam has a less rugged feeling and moves/falls very little compared to a granular high water-absorption resin, and hence it is soft and can possible to be softened and thinned. If the film or foam is incorporated into a nonwoven fabric, it can be easy to arrange the film or foam with various absorption amounts in the plane of the absorbent.

DESCRIPTION OF THE REFERENCE NUMERALS 1 absorbent
2 liquid-permeable topsheet
3 liquid-impermeable backsheet
4 sodium alginate film
5 water-soluble calcium salt composite sheet
6 sodium alginate foam
7 polyvinyl alcohol film
8 gelated product

DETAILED DESCRIPTION OF THE INVENTION

Hereinafter, the present invention is described in detail.

The gelation material serving as an absorbent material constituting the absorbent of the present invention is not particularly limited as long as the material is a polysaccharide capable of being thickened in the presence of a polyvalent metal ion. The material is a polysaccharide which becomes viscous or gelates when dissolved in water and is capable of being thickened, and the polysaccharide is crosslinked when water is absorbed. Examples of the polysaccharides include sodium alginate, propylene glycol alginate, pectin, gellan gum, carrageenan, glucomannan, guar gum, locust bean gum, xanthan gum, glucose, carboxymethyl starch, mannose, galactose, arabinose, fucose, ribose, fructose, dextran and the like. Of those, preferred are sodium alginate, propylene glycol alginate, pectin, gellan gum, carrageenan, glucomannan, and guar gum. Sodium alginate, which is easily obtainable, is particularly preferred.

Sodium alginate is a polysaccharide produced from marine algae and is a major component of fiber in marine algae. When sodium alginate is dissolved in water, the compound is thickened and becomes a sol, while, when sodium alginate is reacted with a polyvalent metal ion, the component may form a gel. Sodium alginate is a linear polysaccharide which includes two kinds of uronic acids, $\beta$-$(1\rightarrow 4)$-D-mannuronic acid (M-block) and α-(1→4)-L-gluconic acid (G-block), and includes M-block including only M-M bonds, G-block including only G-G bonds, and random-block where M and G are randomly arranged. The properties of a gel significantly vary depending on the ratio of M-block and G-block. Sodium alginate is derived from natural products, and hence the compound is biodegradable and biotec safety.

In addition, sodium alginate has properties such as liquid flowability-lowering ability, adherence property, and low friction property, and the compound is widely used for various applications such as food additives, pastes, drugs, cosmetics, wound dressings and the like.

The viscosity grade of sodium alginate is not particularly limited, and high viscosity is desirable for easily achieving high thickening effect and gel strength. Preferable viscosity is 100 mPa·s or more in an aqueous solution of 1% sodium alginate, more preferably 500 mPa·s or more.

The polysaccharide constituting the absorbent of the present invention may have any form such as powder, fiber, film, foam, or composite obtained by immobilizing the polysaccharide on a substrate. The absorbents may include two or more polysaccharides in such forms, and the polysaccharides may be arranged in the absorbent in at least one form.

In the case of using a polysaccharide in the form of powder, a commercially available product may be used as it is, but tends to aggregate if the particle size is small. Therefore, to prevent aggregation, the powder may be coated with an organic solvent or a surfactant, or may be granulated to control the particle size. Examples of the organic solvent which can be used include lower alcohols such as methyl alcohol, ethyl alcohol, propyl alcohol and the like.

If the polysaccharide is in the form of fiber, it may have any shape and may be produced by any method. For example, the polysaccharide in the form of fiber may be produced by spinning and drying the material.

A polysaccharide in the form of film may be produced by forming a material into a film and drying to form a sheet-like film.

If the polysaccharide is in the form of foam, it may have any shape and may be produced by any method. For example, the polysaccharide in the form of foam may be produced by preparing a polysaccharide solution incorporating foams therein by using a foaming agent or gas and a foam stabilizer, forming a film, and drying the resultant film. The foaming ratio is not particularly limited, and the volume may be increased, for example, several times to several tens of times by foaming.

Any polysaccharide in the form of composite may be used as long as it is produced by immobilizing a polysaccharide on a substrate or supporting material with or without a binder material. In the case of using the binder material, the material may have any form as long as the binder material does not inhibit dissolution of the polysaccharide when contacting with a liquid such as a body fluid. For example, the composite may be produced by (A) immobilizing a powder with a binder material on a substrate, (B) immobilizing a fiber with a binder material on a substrate, (C) immobilizing a film with a binder material on a substrate, or (D) immobilizing a foam with a binder material on a substrate. Examples of the binder which can be used include starch, carboxymethyl cellulose, polyvinyl alcohol, and the like, which can act as water-soluble adhesive agents, but other water-soluble polymers may be used. The substrate and support may be films, sheets, films with pores, sheets with pores, films with slits, sheets with slits, ripped films, ripped sheets, woven fabrics, nonwoven fabrics, knitted products, nets, and the like, as long as the substrate and support do not inhibit dissolution of the polysaccharide when contacting with a liquid such as a body fluid.

The substance capable of supplying a polyvalent metal ion constituting the absorbent of the present invention is not particularly limited as long as the substance can supply a polyvalent metal ion which is capable of thickening the polysaccharide. Polyvalent metal ions which has two or more valences include a calcium ion and an aluminum ion, for example. Compounds capable of providing these ions include water-soluble calcium salts such as calcium chloride, calcium lactate, calcium gluconate, calcium acetate and the like, and water-soluble aluminum salts such as aluminum sulfate, aluminum nitrate, aluminum phosphate, aluminum acetate and the like. Preferred is calcium chloride which is easily obtainable.

The substance capable of supplying a polyvalent metal ion constituting the absorbent of the present invention may have any form such as powder or composite. Examples of the powder include a polyvalent metal salt powder coated with an organic solvent, surfactant, gelatin, oblate or the like, and a polyvalent metal salt powder coated with a microcapsule or the like. There can be used known coating agent and microcapsule-forming agent, and any agent can be used as long as dissolution occurs when contacting with a liquid such as a body fluid. If the coating agent and microcapsule-forming agent are selected as agents for adjusting the dissolution rate, the dissolution rate of the substance capable of supplying a polyvalent metal ion can be freely adjusted according to the intended use of the absorbent.

The composite of the substance capable of supplying a polyvalent metal ion may be produced by any method, such as a method of immobilizing the substance on a substrate or supporting material with or without a binder. For example, the composite may be produced by immobilizing a powder of a calcium salt which is a substance capable of supplying a polyvalent metal ion on a substrate with a binder material, or applying an aqueous solution of a calcium salt which is a substance capable of supplying a polyvalent metal ion to a substrate and drying the resultant to immobilize the calcium salt on the substrate. It is also preferable to add into a hot melt adhesive agent. The material to be used for producing a composite should not completely inhibit elution of a polyvalent metal ion when contacting with a liquid such as a body fluid, but the material desirably elutes the polyvalent metal ion while the material is gradually dissolved. The dissolution rate of the substance capable of supplying a polyvalent metal ion may be freely adjusted according to the intended use of the absorbent.

Any material and any form may be used as the substrate constituting the absorbent of the present invention as long as the substrate can be arranged and retained with the substance capable of supplying a polysaccharide or a polyvalent metal ion. It is preferable to use a water-disintegrable or biodegradable substrate as a material. For example, there are forms of fiber, nonwoven fabric, film, sheet and the like. Examples of the fibers include synthetic fibers such as polyethylene, polypropylene, polyethylene terephthalate, polyethylene/polypropylene composite fiber, polyethylene/polyethylene terephthalate composite fiber, polyvinyl alcohol, and polyacrylonitrile, and natural fibers and cellulose-based fibers as regenerated fibers such as pulp, rayon, and acetate. Either single fiber or continuous fiber may be used, the fiber with any fiber diameter also may be used.

As the nonwoven fabric used for a substrate constituting the absorbent of the present invention, various known nonwoven fabrics such as dry-laid or wet-laid nonwoven fabrics produced by through-air, point-bond, or spunlace, spunbond nonwoven fabrics, melt-blow nonwoven fabrics, spunbond/melt-blow/spunbond nonwoven fabrics and the like can be used.

The fiber for forming the nonwoven fabric may be produced from thermoplastic synthetic resin fibers, semisynthetic fibers, and regenerated fibers; or composite fibers obtained by mixing these fibers. While not specified, polyester-based, polyacrylonitrile-based, polyvinylchloride-based, polyethylene-based, polypropylene-based, and polystyrene-based synthetic fibers may be used as the synthetic resin fiber. It is also possible to use, as the synthetic resin fiber, a core-sheath-type composite fiber, a parallel-type composite fiber, a modified hollow fiber, a microporous fiber, or a conjugative type composite fiber. As the semi-synthetic fibers or regenerated fibers cellulose-based or protein-based fibers may be used.

The nonwoven fabrics may have elastically stretchable property. As the stretchable nonwoven fabrics nonwoven fabrics produced by methods such as melt blown and spunbond may be used. The stretchable nonwoven fabrics may be produced from stretchable fibers obtained by melting and spinning a thermoplastic elastomer resin.

The film to be used as a substrate constituting the absorbent of the present invention may have any form, and the film may be a breathable or non-breathable film or a porous film such as a composite film including a high-density polyethylene/low-density polyethylene. The film may be made of same material as the above fiber. Meanwhile, a water-disintegrable tissue paper may also be used as the substrate.

The liquid-permeable topsheet used in the present invention is not particularly limited as long as a liquid can permeate through the sheet. For Example, as the liquid-impermeable topsheet any of a hydrophilic fiber nonwoven fabric, a hydrophobic fiber nonwoven fabric with many pores, and a plastic film with pores may be used.

The liquid-impermeable backsheet is not particularly limited as long as a liquid cannot permeate through the sheet. For example, a film or a nonwoven fabric may be used as the liquid-impermeable backsheet.

The polysaccharide and the substance capable of supplying a polyvalent metal ion constituting the absorbent of the present invention are not only incorporated in a substrate, but may also be formed into film-like or sheet-like products from these own. In the latter case, the product may be produced by forming an aqueous solution of the polysaccharide into a film and drying the film. In the case of using the substance capable of supplying a polyvalent metal ion, the film- or sheet-like product may also be obtained in the same manner as the above procedure of the polysaccharide. The mass per unit area and thickness may be appropriately adjusted. If the mass per unit area and thickness is too small, the effect of lowering flowability achieved by increased viscosity is low, while if the mass per unit area and thickness is too large, the product is increased in weight and volume and thus wearing comfortability and portability may become worse. The appropriate mass per unit area and thickness may be determined according to the type and intended use of the absorptive article comprising the absorbent. The optimum mass per unit area and thickness may preferably be determined in the ranges of 10 to 1,000 gsm (g/m$^2$) and 10 µm to 20 mm, respectively.

In general, the film-like or sheet-like product comprising the polysaccharide and the substance capable of supplying a polyvalent metal ion has a flat and smooth shape with a constant thickness, but the product may have irregularities formed by embossing or may have a three-dimensional structure. Moreover, the product may have pores with various shapes or cuts of a noncontiguous pattern such as zigzag alignment or may be crushed flakes. In addition, the product may include a single layer or two or more layers. The densities and materials of the respective layers which are laminated may be changed to control the dissolution rate and dissolution amount, for example.

In addition to the polysaccharides, the absorbent of the present invention may comprise various additives which are usually used, such as thickeners, plasticizers, flavors, deodorants, various inorganic powders, pigments, dyes, antibacterial agents, and adhesives. Examples of the thickeners include polyvinyl alcohol and polyacrylic acid, and examples of the plasticizers include glycerol, sorbitol, lactitose, maltitose, erythritol, pentaerythritose and the like. Trehalose can be also used to prevent the films and the sheets from cracking due to drying. Those additives can provide the absorbent material with various functions. The inorganic powders to be used may be any inorganic powders as long as it is inert to liquid, and examples thereof include silicon dioxide, zeolite, kaolin, clay and the like.

The structure of the absorbent of the present invention is not particularly limited as long as the structure consists essentially of a polysaccharide capable of being thickened in the presence of a polyvalent metal ion and a substance capable of supplying the polyvalent metal ion. For example, the absorbent may have a structure such as a structure obtained by cutting and mixing a film-like or sheet-like product comprising a polysaccharide and a substance capable of supplying a polyvalent metal ion, or a structure crushing and mixing the film-like or sheet-like product. In this case, the polysaccharide is dissolved by a body fluid or liquid excreta, dissolution of the substance capable of supplying the polyvalent metal ion is simultaneously started to supply the polyvalent metal ion, which causes gelation of the polysaccharide.

The absorbent of the present invention may have any shape and arrangement as long as the absorbent has a structure in which the polysaccharide capable of being thickened and the substance capable of supplying a polyvalent metal ion can be used in combination so that the polysaccharide is thickened and gelated by the polyvalent metal ion supplied from the substance capable of supplying a polyvalent metal ion. The aspects of the structure of the absorbent are described below.

(1) A structure obtained by arranging a sheet/composite/foam/fiber containing or comprising a polysaccharide on the skin contacting side where a body fluid or liquid excreta enters into and a substance capable of supplying a polyvalent metal ion on the skin non-contacting side.

(2) A structure obtained by arranging a sheet/composite/foam/fiber containing or comprising a polysaccharide on the skin contacting side and substances capable of supplying a polyvalent metal ion on the skin non-contacting side and on the skin contacting side.

(3) A structure obtained by arranging a sheet/composite/foam/fiber containing or comprising a polysaccharide on the skin non-contacting side and a substance capable of supplying a polyvalent metal ion on the skin contacting side.

In the absorbents of (2) and (3), in the case where the substance capable of supplying a polyvalent metal ion is arranged on the skin contacting side, it is necessary to modified the material and/or the structure (such as formation of pores, partially arrangement) for preventing inhibition of permeation of a body fluid and dissolution of the polysaccharide.

(4) A structure obtained by wrapping the substance capable of supplying a polyvalent metal ion with the sheet/composite/foam/fiber containing or comprising a polysaccharide.

(5) A structure obtained by arranging a structure produced by wrapping the substance capable of supplying a polyvalent metal ion with the sheet/composite/foam/fiber containing or comprising a polysaccharide on the top and bottom or on the right and left sides of the absorbent.

(6) A structure obtained by mixing a powder containing or comprising the polysaccharide with a powder of the substance capable of supplying a polyvalent metal ion having an adjusted dissolution rate.

(7) A structure obtained by sandwiching the substance capable of supplying a water-soluble polyvalent metal ion between sheets containing or comprising the polysaccharide.

(8) A structure obtained by sandwiching the substance capable of supplying a water-soluble polyvalent metal ion between sheets containing or comprising the polysaccharide and laminating a plurality of the resultant sandwiches.

The structure and arrangement of the absorptive article of the present invention are not particularly limited as long as the above-mentioned absorbent can absorb a body fluid or liquid excreta in an effective manner. The aspects of the absorptive article are described below.

(a) An absorptive article which has a liquid-permeable topsheet, a liquid-impermeable backsheet, and an absorbent positioned between the both sheets.

(b) An absorptive article which has a liquid-permeable topsheet, a liquid-impermeable backsheet, and an absorbent positioned between the both sheets, and further has a material for assisting dispersion and/or water absorption which is arranged in the absorbent, and/or between the topsheet and absorbent, and/or between the absorbent and backsheet.

(c) An absorptive article in which at least one of the liquid-permeable topsheet and liquid-impermeable backsheet is water-disintegrable.

(d) An absorptive article in which at least one of the liquid-permeable topsheet and liquid-impermeable backsheet is biodegradable.

Examples of the material for assisting dispersion and/or water absorption which can be used in the present invention include a pulp and a high water-absorption resin.

The absorbent of the present invention has excellent absorbability, and thus can be used for various applications which require water absorption or water retention, including: sanitary goods such as sanitary napkins and panty liners; hygiene products such as disposable diapers, sheets for preventing urine leakage, and urine absorption pads for patients with incontinence; medical supplies for absorption of body fluid/blood; wound dressings; cosmetic packs; animal excreta-treating materials; agricultural and garden supplies; goods used in the food field such as freshness-keeping materials; and dew condensation preventing materials. The present invention also relates to an absorptive article including any of the above-mentioned absorbents.

Figure 1:
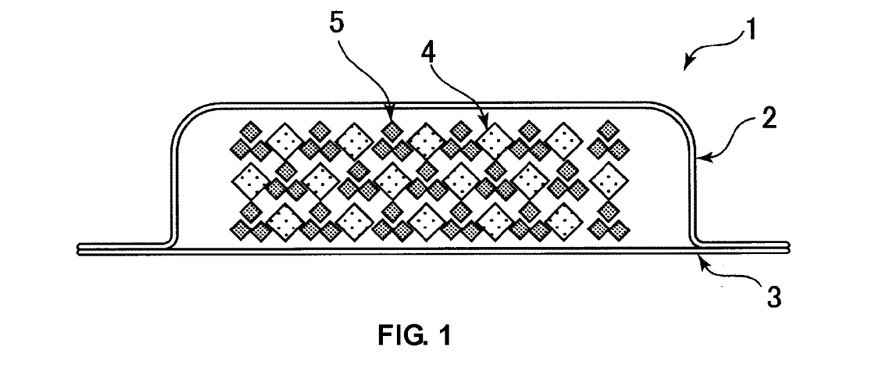
FIG. 1 shows a cross-sectional view of an absorbent of Example 1.
Figure 2:
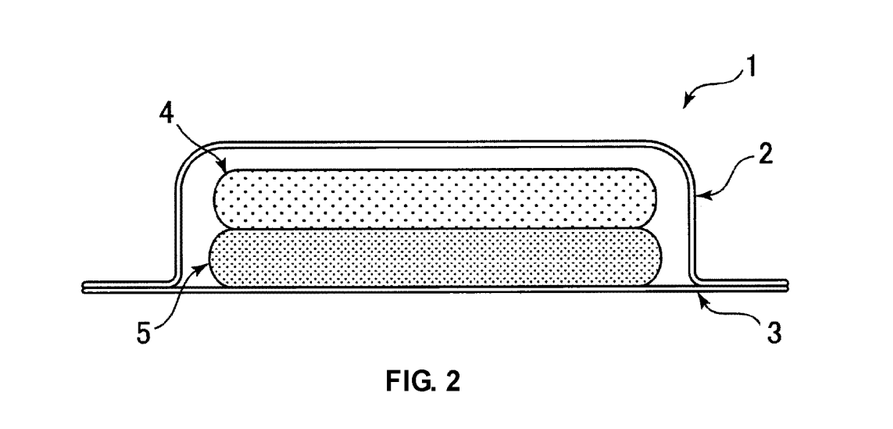
FIG. 2 shows a cross-sectional view of an absorbent of Example 2.
Figure 3:
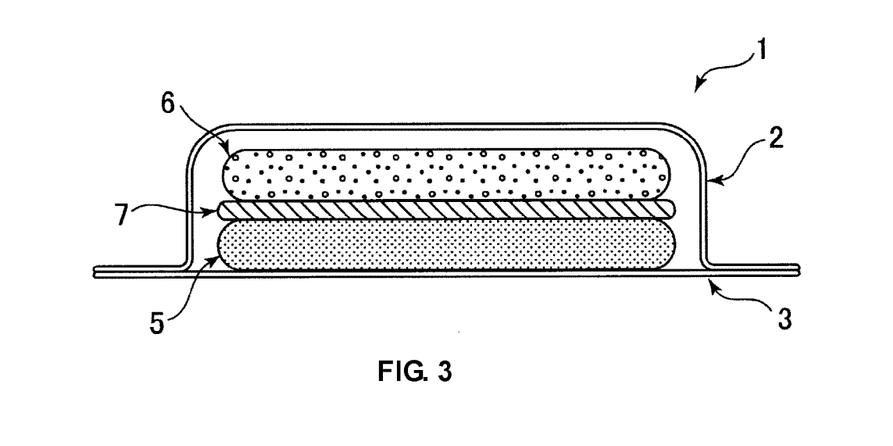
FIG. 3 shows a cross-sectional view of an absorbent of Example 3.
Figure 4:
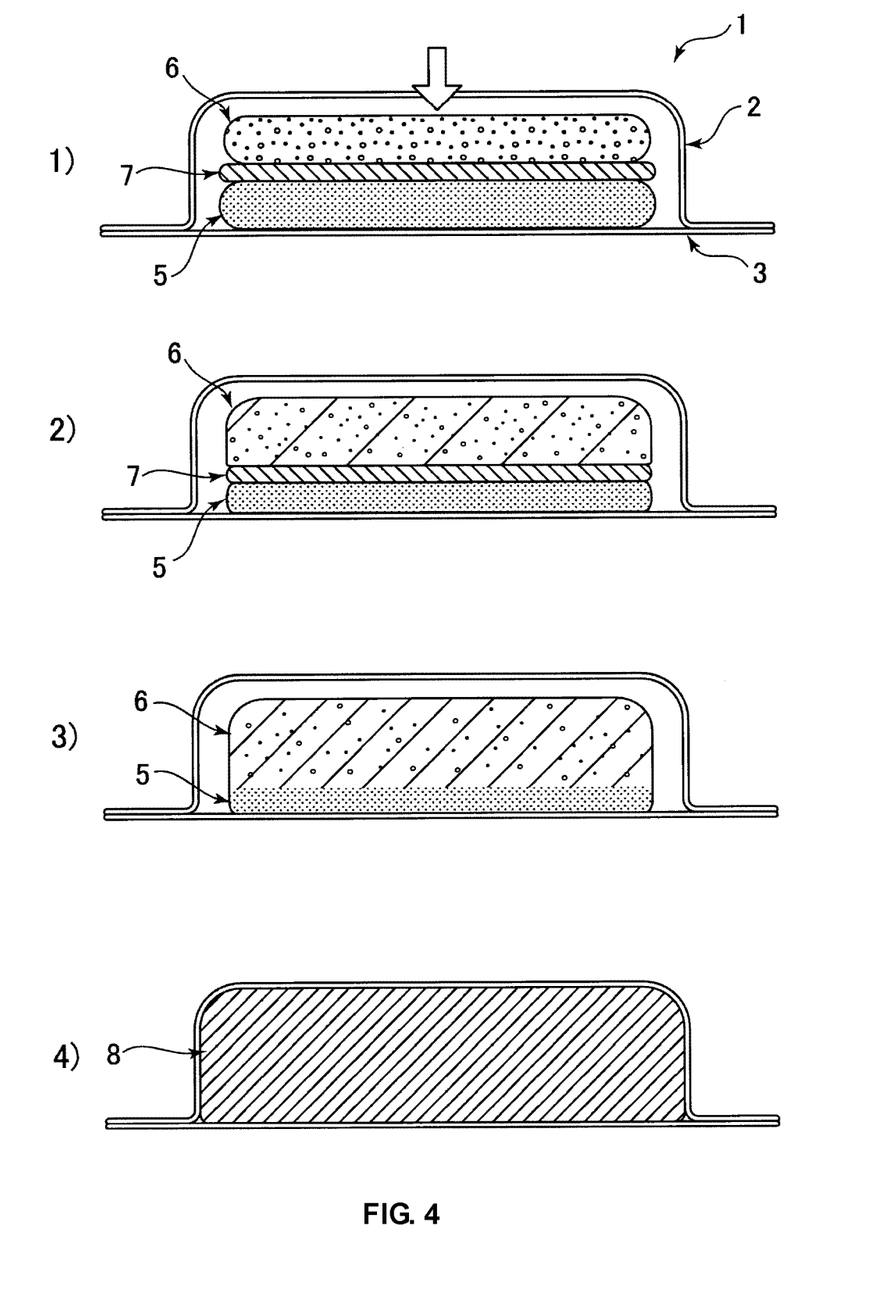
FIG. 4 shows a drawing illustrating an action of an absorbent of the present invention.

FIG. 1 is a cross-sectional view of an absorbent 1 illustrating an aspect of Example 1 of the present invention. FIG. 2 is a cross-sectional view of an absorbent 1 illustrating an aspect of Example 2 of the present invention. FIG. 3 is a cross-sectional view of an absorbent 1 illustrating an aspect of Example 3 of the present invention. FIG. 4 is a cross-sectional view of the absorbent of Example 3, which illustrates the action of the absorbent step-by-step.

FIG. 1 is a cross-sectional view of the absorbent 1 illustrating the aspect of Example 1 of the present invention. The absorbent 1 is formed by: randomly arranging a sodium alginate film 4 and a water-soluble calcium salt composite sheet 5, those of which are cut into several centimeters square pieces, on a liquid-impermeable backsheet 3; covering the pieces on the backsheet with a liquid-permeable topsheet 2; and bonding the peripheries.

FIG. 2 is a cross-sectional view of the absorbent 1 illustrating the aspect of Example 2 of the present invention. The absorbent 1 is formed by: arranging the water-soluble calcium salt composite sheet 5 and sodium alginate film 4 in this order on the liquid-impermeable backsheet 3; covering the film and the sheet with the liquid-permeable topsheet 2; and bonding the peripheries.

FIG. 3 is a cross-sectional view of the absorbent 1 illustrating the aspect of Example 3 of the present invention. The absorbent 1 is formed by: arranging the water-soluble calcium salt composite sheet 5, a polyvinyl alcohol sheet 7, and a sodium alginate foam 6 in this order on the liquid-impermeable backsheet 3; covering the sheets and the foam with the liquid-permeable topsheet 2; and bonding the peripheries. The liquid-permeable topsheet 2 corresponds to the skin contacting side.

The action of the absorbent of the present invention will be described below. The absorbent 1 of Example 3 shown in FIG. 3 is used in FIG. 4. The sodium alginate foam 6 is used as a polysaccharide capable of being thickened in the presence of a polyvalent metal ion and the polyvinyl alcohol film 7 is arranged between the sodium alginate foam 6 and the water-soluble calcium salt composite sheet 5 so that the sodium alginate foam 6 does not come into contact directly with the water-soluble calcium salt composite sheet 5 which is a substance capable of supplying a polyvalent metal ion. The absorbent 1 is formed by: arranging the water-soluble calcium salt composite sheet 5, the polyvinyl alcohol sheet 7, and the sodium alginate foam 6 on the liquid-impermeable backsheet 3 in this order; wrapping the upper surface of the layers with the liquid-permeable topsheet 2; and bonding the peripheries of the topsheet 2 and the liquid-impermeable backsheet 3 by fusion bonding or with an adhesive agent.

The action of the absorbent is as follows.

1) A body fluid permeates the absorbent 1 through the liquid-permeable topsheet 2.

2) The permeated body fluid causes dissolution/swelling of sodium alginate parts in the sodium alginate foam 6 which is positioned on the skin contacting side.

3) The permeated body fluid further arrives at the water-soluble polyvinyl alcohol sheet 7 to cause dissolution of the polyvinyl alcohol sheet 7. At the same time, dissolution of the water-soluble calcium salt composite sheet 5 is started following the dissolution and swelling of sodium alginate. Swelling of sodium alginate is almost completed before dissolution of the calcium salt is started.

4) As soon as the calcium ion is reacted with swollen sodium alginate, gelation is started immediately to form a gelated product 8, thereby the body fluid can be retained.

EXAMPLES

Hereinafter, the present invention is described in detail by way of examples, but is not limited to the examples. In all following examples, a through-air nonwoven fabric and a polyethylene film were used as a topsheet and a backsheet, respectively.

Example 1

As a polysaccharide capable of being thickened in the presence of a polyvalent metal ion, an aqueous solution of 5% sodium alginate (80 to 120 mPa·c, manufactured by Wako Pure Chemicals Industries, Ltd., extra pure reagent) was applied to a stainless-steel plate in an amount of 300 gsm (containing 15 gsm of sodium alginate), dried at 70° C. for 3 hours to produce a sodium alginate film 4 with a size of 100 mm square and a thickness of 1.2 mm. Subsequently, as a substance capable of supplying a polyvalent metal ion, an aqueous solution of 20% calcium chloride was applied to an SB nonwoven fabric (ELTAS AQUA, manufactured by Asahi Kasei Corporation, 20 gsm) in an amount of 100 gsm (containing 20 gsm of calcium chloride) and dried at 70° C. for 3 hours to produce a water-soluble calcium salt composite sheet 5. Both the film and the sheet were cut into 1 cm square pieces and mixed to produce an absorbent material, and the resultant material was randomly arranged in an area of 5 cm square on a liquid-impermeable backsheet 3 and wrapped with a liquid-permeable topsheet 2. Then, the peripheries were bonded, to thereby produce an absorbent 1 (Example 1) shown in FIG. 1.

Example 2

The sodium alginate film 4 and the water-soluble calcium salt composite sheet 5 produced in Example 1 were used to produce an absorbent 1 in which the sodium alginate film 4 was arranged on the skin contacting side and the water-soluble calcium salt composite sheet 5 was arranged on the skin non-contacting side. That is, the water-soluble calcium salt composite sheet 5 and sodium alginate film 4 were arranged in this order on the liquid-impermeable backsheet 3 and wrapped with the liquid-permeable topsheet 2. Then, the peripheries were bonded, to thereby produce an absorbent 1 (Example 2) shown in FIG. 2.

Example 3

As a polysaccharide capable of being thickened in the presence of a polyvalent metal ion 100 g of aqueous solution of 3% sodium alginate (B-S, manufactured by KIMICA Corporation) was added to 3 g of DICRYLAN FOAMER HP (manufactured by Huntsman Textile Effects GmbH) to form foams until the foaming ratio reached 5, and the resultant foam was applied in a thickness of 10 mm on a stainless-steel plate and dried at 70° C., to thereby produce a sodium alginate foam 6. Subsequently, a polyvinyl alcohol film 7 (Hi-Selon M-250, manufactured by The Nippon Synthetic Chemical Industry, Co., Ltd.) was arranged between the sodium alginate foam 6 and water-soluble calcium salt composite sheet 6 which was produced in Example 1 as the substance capable of supplying a polyvalent metal ion so that the sodium alginate foam 6 would not be directly brought into contact with the water-soluble calcium salt composite sheet 5. The water-soluble calcium salt composite sheet 5, the sodium alginate foam 6, and the polyvinyl alcohol film 7 were separately cut into 5-cm square pieces to produce an absorbent. That is, the water-soluble calcium salt composite sheet 5, the polyvinyl alcohol film 7, and the sodium alginate film 4 were arranged in this order on the liquid-impermeable backsheet 3, and wrapped with the liquid-permeable topsheet 2. Then, the peripheries were bonded, to thereby produce an absorbent 1 (Example 3) shown in FIG. 3.

Comparative Example 1

An absorbent was produced in the same manner as in Example 2, except that the positions of the sodium alginate film 4 and the water-soluble calcium salt composite sheet 5 were reversed. That is, the water-soluble calcium salt composite sheet 5 was arranged on the skin contacting side, and the sodium alginate film 4 was arranged on the skin non-contacting side. Specifically, the sodium alginate film 4 and the water-soluble calcium salt composite sheet 5 were arranged in this order on the liquid-impermeable backsheet 3, followed by the same procedures as above, to thereby produce an absorbent (Comparative Example 1).

Comparative Example 2

An absorbent (Comparative Example 2) was produced in the same manner as in Example 2, except that only theسodium alginate film 4 was arranged on the liquid-impermeable backsheet 3.

Comparative Example 3

The same procedures of Example 1 were repeated except that absorbent materials obtained by uniformly mixing and laminating 200 gsm of a pulp (NB-416, manufactured by Weyerhaeuser Company) and 200 gsm of a high water-absorbent resin (SA60S, manufactured by Sumitomo Seika Chemicals Co., Ltd.) was cut into 5-cm square pieces. The absorbent materials were then arranged randomly in an area of 5-cm square on the liquid-impermeable backsheet 3 and wrapped with the liquid-permeable topsheet 2, followed by bonding the peripheries, to thereby produce an absorbent (Comparative Example 3).

Comparative Example 4

The same procedures of Example 1 were repeated except that 100 gsm of a high-absorbent resin (SA60S, manufactured by Sumitomo Seika Chemicals Co., Ltd.) was cut into 5-cm square pieces, and the pieces were arranged uniformly on the liquid-impermeable backsheet 3 and wrapped with the liquid-permeable topsheet 2, followed by bonding the edges, to thereby prepare an absorbent (Comparative Example 4).

The absorbents both of examples and comparative examples were evaluated for only the absorbent portions in the state of not using the liquid-permeable topsheet and liquid-impermeable backsheet parts by determining the absorbency and gel strength.

Absorbency: an absorbent portion was added to 30 g of artificial urine and allowed to stand for 30 minutes, and the mass of the sample was determined as "absorption amount" and compared to that of the sample before absorption.

Absorbency=sample weigh after absorption/sample weigh

Determination of gel strength: a container (diameter: 12 mm, height: 8 mm) was filled with a gel produced, and the strength at the moment of contact with the gel was determined using a digital force gauge (FGC-0.2, manufactured by SHIMPO, diameter of a terminal: 8 mm, depression speed: 4 cm/min).

Note that the artificial urine is an aqueous solution of 2% by mass of urea, 0.8% by mass of sodium chloride, 0.08% by mass of magnesium sulfate heptahydrate and 0.03% by mass of calcium chloride dihydrate.

The results of examples and comparative examples are shown in Table 1.

TABLE 1

|  | Sample mass (g) | Mass after absorption (g) | Absorbency (g/g) | Gel strength (N) |
|---|---|---|---|---|
| Example 1 | 0.039 | 0.79 | 20.3 | 0.16 |
| Example 2 | 0.042 | 1.35 | 32.1 | 0.29 |
| Example 3 | 0.290 | 7.21 | 24.9 | 0.21 |

TABLE 1-continued

|  | Sample mass (g) | Mass after absorption (g) | Absorbency (g/g) | Gel strength (N) |
|---|---|---|---|---|
| Comparative Example 1 | 0.036 | 0.31 | 8.6 | 0.12 |
| Comparative Example 2 | 0.040 | 0.85 | 21.3 | No gelation |
| Comparative Example 3 | 1.100 | 21.48 | 19.5 | 0.26 |
| Comparative Example 4 | 0.270 | 2.45 | 9.1 | 0.26 |

The "sample mass" means the mass of sodium alginate alone.

The absorbents of Examples 1 to 3 were found to be useful because the absorption capacity (rate) were larger than the absorption capacity (rate) of the absorbent of Comparative Example 3 which is a conventional high water-absorbent resin. Among the absorbents of Examples 1 to 3, the absorbent of Example 2 was found to have the best in both absorption capacity (rate) and gel strength. From the comparison of Example 3 and Comparative Example 3, the absorption capacity (rate) of Example 3 was found to be higher by about 28% (=24.9/19.5) than that of Comparative Example 3. The gel strength is desirably 0.1 N or more in view of the body pressures of babies, and in the cases of Examples 1 to 3, gels with sufficiently high strengths were formed.

The absorbent of Comparative Example 1 is produced in the same manner as Example 2 except that the sodium alginate film and the water-soluble calcium salt composite sheet are reversely arranged. The absorbent of Comparative Example 1 was not a satisfactory one because the absorption capacity (rate) and the gel strength were low. As the absorbent of Comparative Example 2 includes only the sodium alginate film, no gel was formed although dissolution occurred. The absorbent of Comparative Example 4 was found to have a certain degree of gel strength but have low absorption capacity (rate).

INDUSTRIAL APPLICABILITY

According to the present invention, it is possible to reduce the amount of an absorbent material used and to achieve reductions in the weight and thickness of the absorptive article because the absorbent of the present invention has a structure designed so that a polysaccharide capable of being thickened in the presence of a polyvalent metal ion can be dissolved and swollen by a body fluid or liquid excreta, at the same time the polysaccharide thickened with the polyvalent metal ion can absorb a large amount of the body fluid or liquid excreta. Moreover, after the swelling of the polysaccharide was developed, the polysaccharide is crosslinked by the polyvalent metal ion to thereby completely retain the body fluid or the like in a gel state, and thus the absorbent can lower flowability of the liquid and can prevent return and leakage of the liquid. Therefore, the present invention can be used as an absorbent useful for various fields and an absorptive article containing the absorbent.

What is claimed is:

1. An absorbent comprising at least a polysaccharide capable of being thickened in a presence of a polyvalent metal ion and a substance capable of supplying the polyvalent metal ion when contacted with a body fluid, wherein the polysaccharide is arranged at a position where the polysaccharide is brought into contact with a body fluid before the substance capable of supplying the polyvalent metal ion is brought into contact with the body fluid and the substance capable of supplying the polyvalent metal ion is subjected to one of a coating or microcapsulation treatment for adjusting a dissolution rate of the polyvalent metal ion upon contact with a body fluid.

2. An absorbent according to claim 1, wherein dissolution of the substance capable of supplying the polyvalent metal ion is started after dissolution of the polysaccharide.

3. An absorbent according to claim 1, wherein the polysaccharide is arranged in the absorbent in at least one form selected from the group consisting of a foam, a film, a immobilized substrate, powder and a fiber.

4. An absorbent according to claim 1, wherein the polysaccharide comprises at least one selected from the group consisting of sodium alginate, propylene glycol alginate, pectin, gellan gum, carrageenan, glucomannan and guar gum.

5. An absorbent according to claim 1, wherein the substance capable of supplying the polyvalent metal ion is a substance capable of supplying a divalent metal ion.

6. An absorptive article comprising a liquid-permeable topsheet, a liquid-impermeable backsheet, and the absorbent according to claim 1 located between the sheets.

7. An absorptive article according to claim 6, further comprising a material for assisting dispersion and/or water absorption arranged in the absorbent, and/or between the topsheet and absorbent, and/or between the absorbent and backsheet.

8. An absorptive article according to claim 6, further having water-disintegrability.

9. An absorptive article according to claim 6, further having biodegradability.

* * * * *